US006087176A

United States Patent [19]
Durzan et al.

[11] Patent Number: 6,087,176
[45] Date of Patent: *Jul. 11, 2000

[54] CYCLODEXTRINS IN PLANT NUTRIENT FORMULATIONS

[75] Inventors: Don J. Durzan; Frank F. Ventimiglia, both of Davis, Calif.

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/599,960

[22] Filed: Feb. 14, 1996

[51] Int. Cl.[7] ..................................................... C12N 5/00
[52] U.S. Cl. ........................... 435/431; 435/410; 435/420
[58] Field of Search .................................... 435/410, 420, 435/431; 47/1.01

[56] References Cited

U.S. PATENT DOCUMENTS

| | | | |
|---|---|---|---|
| 4,272,276 | 6/1981 | Szejtli et al. | 504/292 |
| 4,380,626 | 4/1983 | Szejtli et al. | 536/103 |
| 4,797,153 | 1/1989 | Yokoyama et al. | 504/326 |
| 4,923,853 | 5/1990 | Szejtli et al. | 514/58 |
| 5,547,866 | 8/1996 | Durzan et al. | 435/123 |

OTHER PUBLICATIONS

Wenz, G., "Cyclodextrins as building blocks for supramolecular structures and functional units," Agnew. Chem. Int. Ed. Engl. 33:803–822 (1994).

Woerdenbag, H.J. et al., "Increased podophyllotoxin production in *Podophyllum hexandrum* cell suspension cultures after feeding coniferyl alcohol as a alpha–cyclodextrin complex," Plant Cell Reports 9:97–100 (1990).

Szejtli, J., "Cyclodextrins and their inclusion complexes," Akademiai Kiado, Budapest 219–255 (198) . (1998).

Szejtli, J., "Cyclodextrin Technology," Topics in Inclusion Science, Chapter 2, pp. 77–185, Kluwer Academic Publishers.

Bender, M.L. et al., "Catalyses by cyclodextrins leading to practical usages of cyclodextrins," Chapter IV, pp. 27–86, Cyclodextrin Chemistry.

Hashimoto, H., "Preparation, structure, property and application of branched cyclodextrins," Chapter 3, *New trends in cyclodextrins and derivatives*, pp. 97–156.

Hedges, A.R. et al., "Complexation in modified cyclodextrin compared with unmodified cyclodextrin," Chapter 8, *New trends in cyclodextrins and derivatives*, pp. 297–311.

Szejtli, J., "The use of cyclodextrins in biotechnological operations," Chapter 17, *New trends in cyclodextrins and derivatives*, pp. 595–625.

*Primary Examiner*—Leon B. Lankford, Jr.
*Attorney, Agent, or Firm*—Townsend and Townsend and Crew LLP

[57] ABSTRACT

The present invention provides new plant nutrient formulations comprising cyclodextrins. The formulations are useful, for instance, in increasing growth, cellular development and secondary metabolite production of plant tissue cultures.

23 Claims, No Drawings

CYCLODEXTRINS IN PLANT NUTRIENT FORMULATIONS

FIELD OF THE INVENTION

The present invention is directed to improved methods for culturing plant cells. In particular it relates to the use of cyclodextrins in plant nutrient formulations, such as tissue culture media and hydroponic solutions.

BACKGROUND OF THE INVENTION

Plant cells and explants grown in vitro find a number of uses. For instance, cultivars with desired traits (e.g., herbicide resistance) can be more easily selected in vitro than by using whole plants. Totipotent tissue culture cells are then used to regenerate whole plants with desired characteristics. Transgenic plants can be obtained by incubating plant cells or explants with appropriate vectors capable of inserting foreign DNA into the plant genome before regenerating whole plants. Plant tissue culture cells are also useful for the production of various plant secondary metabolites which have use in a variety of contexts.

Generally, methods of plant cell tissue culture have been developed for use with angiosperms, such as tobacco. Gymnosperms, however, have not been as readily amenable to cell culture and plant regeneration. Among conifers, members of the genus Taxus are of particular interest because of their production of taxol and related taxanes. Taxane compounds, in particular taxol, have significant antitumor activity and have been the focus of investigations to develop these compounds as drugs for the treatment of cancer. These compounds have also been shown to inhibit congenital polycystic kidney disease (Woo et al. *Nature* 368 759 (1994)). Taxol, originally isolated from the bark of the Pacific yew, *Taxus brevifolia*, was recently approved by the Food and Drug Administration for use against ovarian cancer and has also shown activity against breast, lung and other cancers.

Because of the importance of cell culture techniques in many technologies, improved methods for culturing plant cells to increase, for example, the rate of cell doubling, are particularly desirable. The present invention addresses these and other needs.

SUMMARY OF THE INVENTION

The present invention provides methods of contacting plant cells with improved nutrient formulations. The nutrient formulations may be used with whole plants or in tissue culture media used for culturing plants cells. The methods comprise contacting plant cells with a nutrient formulation comprising between about 0.1% and about 10% (w/v) free cyclodextrins and maintaining the plant cells under conditions suitable for growth.

Any plant tissue or cells can be used in the methods of the invention. Plant tissue culture cells from a member of the order Coniferales are conveniently used. Examples include embryogenic Norway spruce (Picea) cultures and drug-producing Pacific Yew (Taxus) cultures. The cyclodextrins can be used to supplement any plant nutrient formulation, examples include tissue culture media such as ½ L.P. medium for conifer cell cultures or hydroponics for plant growth.

A number of cyclodextrins can be used. Examples include hydroxyethyl-β-cyclodextrin, G2-α-cyclodextrin, G2-β-cyclodextrin, hydroxypropyl-β-cyclodextrin, and methyl-β-cyclodextrin. The cyclodextrins are usually at a concentration between about 1.25% and about 5%, often about 2.5% (w/v).

Also provided by the present invention are plant nutrient formulations comprising free cyclodextrin at a concentration between about 0.1% and about 10% (w/v).

Definitions

The term "plant" includes whole plants, plant organs (e.g., leaves, stems, roots, flowers, etc.), seeds, plant tissue culture cells derived from any plant organ or tissue and progeny of same. The class of plants which can be used in the methods of the invention is generally as broad as the class of seed plants amenable to tissue culture techniques, including both gymnosperms and angiosperms (including monocotyledonous and dicotyledonous plants).

As used herein the terms "conifer" and "order Coniferales" is used in the standard taxonomic sense to refer to the taxonomic group of gymnosperms generally having well-defined cones. Members of this order are divided among seven plant families: Pinaceae (including e.g., Pinus, Pseudotsuga, Abies, Picea, and Cedrus), Taxodiaceae (including e.g., Taxodium, Metasequoia, and Sequoia), Cupressaceae (including e.g., Cupressus, Juniperus, Thuja, Calocedrus, and Libocedrus), Araucariaceae (including Araucaria and Agathis), Podocarpaceae (including e.g., Podocarpus, Dacrydiun, and Phyllocladus), Cephalotaxaceae (Cephalotaxus), and Taxaceae (including Taxus and Torreya). See, e.g., Lawrence, Taxonomy of Vascular Plants (Macmillan Company, 1951).

The term "plant nutrient formulation" as used herein refers to a solidified or liquid medium, including hydroponic media, used to sustain the growth of whole plants, explants, plant cells or plant tissues. The plants or plant tissues may be maintained in vitro (e.g., micropropagation) or under greenhouse and field conditions. Thus, in some embodiments, the plant nutrient formulations of the invention are plant tissue culture media for culturing plant cells or explants. The plant nutrient formulations of the invention are typically supplemented with nutrients well-known in the art and desirable for the vigorous growth of plants and plant cells.

The term "free cyclodextrin" refers to a cyclodextrin composition, in which the cyclodextrin is initially added to the plant tissue culture medium not complexed with a second molecule. One of skill will recognize that once free cyclodextrins are present in a plant tissue culture medium they may complex with a variety of compounds, for instance, plant secondary metabolites, present in the formulation. As used herein, the term includes random cyclodextrin complexes that occur as a result of the addition of an initially uncomplexed cyclodextrin molecule.

The term "free cyclodextrin", however, specifically excludes compositions in which all or substantially all (at least about 90%) of the cyclodextrin molecules are deliberately complexed with a single species. Such compositions are used to increase solubility or bioavailabilty of a specific compound, for instance, in bioconversions using plant cell tissue cultures. Determination of the percent of cyclodextrins complexed with an individual species can be carried out using a number of techniques known to those of skill in the art. For instance, spectroscopic characterization in the UV to visible range can be used to quantitate the degree of complexation of cyclodextrins to a particular molecular species.

A "plant tissue culture" is a collection of plant cells, tissues or explants grown in vitro. The plant tissue cultures can include totipotent plant cells and tissues which are used to regenerate whole plants in, for instance, procedures and methods used in micropropagation.

The term "haploid cell culture" refers to cell cultures in which each cell contains a single copy of each chromosome, as opposed to diploid or polyploid cells which contain two or more copies of each chromosome. Haploid cells of the invention are typically derived from male or female gametophytic tissue. Gametophytic tissue includes all haploid cells derived from meiosis of the megasporocyte (female gametophyte) or microsporocyte (male gametophyte).

"Haploid-derived" cells are homozygous diploid or polyploid cells which arise from haploid cells either spontaneously or by manipulation of the cultures. Such cells may comprise more than one nucleus and can arise spontaneously in culture, from fusion (spontaneous or induced) of protoplasts derived from the haploid cells, or by treatment of the cells with compounds known to increase ploidy such as colchicine.

DESCRIPTION OF THE PREFERRED EMBODIMENT

The present invention provides new plant nutrient formulations which comprise free cyclodextrins and which are useful for growing plants and plant cells. As shown below, the formulations of the invention lead to increased growth, cellular development, and vigor of plant cells.

The formulations can be applied to growth of plant cells in a variety of contexts. In one embodiment, the formulations are used with plant tissue cultures. The tissue cultures can be derived from any plant tissue suitable for establishing such cultures. Tissue from any part of the plant including bark, cambium, needles, leaves, stems, seeds, fruit or cones and roots may be used.

Although the formulations of the invention are particularly useful for growing conifers, especially Taxus cells, the methods and compositions can be adapted for use in the culture of any plant cells or tissue capable of being grown in vitro. For instance, the invention can be used with species from the genera Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Juglans, Lactuca, Linum, Lolium, Lycopersicon, Malus, Manihot, Majorana, Medicago, Nicotiana, Oryza, Panieum, Pannesetum, Persea, Phaseolus, Pisum, Pyrus, Prunus, Raphanus, Secale, Senecio, Sinapis, Solanum, Sorghum, Trigonella, Triticum, Vitis, Vigna, and, Zea.

The plant tissue cultures of the invention, are maintained in any of a number of standard growth media, many of which are commercially available (e.g., Sigma Chemical Co., St. Louis, Mo.). Examples include Schenk-Hildebrandt (SH) medium, Linsmaier-Skoog (LS) medium, Murashige and Skoog (MS) medium, Gamborg's B5 medium, Nitsch & Nitsch medium, White's medium, Hoagland's solution, and other variations and supplements well known to those of skill in the art (see, e.g., *Plant Cell Culture*, Dixon, ed. IRL Press, Ltd. Oxford (1985) and George et al, *Plant Culture Media*, Vol 1, Formulations and Uses Exegetics Ltd. Wilts, UK, (1987)). For the growth of conifer cells, particularly suitable media include ½ MS, ½ L.P., DCR, Woody Plant Medium (WPM), Gamborg's B5 and its modifications, DV, SH, and White's medium.

Depending upon the desired result (e.g., initiation of callus, embryogenesis, development of shoots, development of roots) these media will be supplemented with or will already contain appropriate plant hormones well known to those of skill in the art and available from, for instance, Sigma Chemical Co. Such hormones include cytokinins (e.g., zeatin and kinetin), auxins (e.g., 2,4-dichlorophenoxyacetic acid (2,4-D), napthaleneacetic acid (NAA), and indole butyric acid (IBA)), gibberellins, betaines and the like.

In addition to standard plant tissue culture media components, the media of the present invention also comprise free cyclodextrins. Cyclodextrins are cyclic oligosaccharides, consisting of 6, 7 or 8 glucose units, designated by the Greek letter $\alpha$, $\beta$ or $\gamma$, respectively. Cyclodextrins with fewer than six glucose units are not known to exist.

The glucose units are linked by $\alpha$-1,4-glucosidic bonds. As a consequence of the chair formation of the sugar units, all secondary hydroxyl groups (at $C_2$, $C_3$) are located on one side of the ring, while all the primary hydroxyl groups at $C_6$ are situated on the other side. As a result, the external faces are hydrophilic, making the cyclodextrins water-soluble. In contrast, the cavities of the cyclodextrins are hydrophobic, since they are lined by the hydrogen of atoms $C_3$ and $C_5$, and by ether-like oxygens. These matrices allow complexation with a variety of relatively hydrophobic compounds, including, for instance, steroid compounds such as 17$\beta$-estradiol (see, e.g., van Uden et al. *Plant Cell Tiss. Org. Cult.* 38:1–3–113 (1994)). The complexation takes place by Van der Waals interactions and by hydrogen bond formation. For a general review of the chemistry of cyclodextrins, see, Wenz, *Agnew. Chem. Int. Ed. Engl.*, 33:803–822 (1994).

Cyclodextrins may be purchased from commercial sources such as Sigma Chemical Co. and Ensuiko Sugar Refining Co., Tokyo, Japan. Cyclodextrins are typically prepared from potato starch. Cyclodextrin-glucosyltransferase, an enzyme that is produced by several bacteria (e.g., Bacillus, Micrococcus and Klebsiella) is used to convert the pre-hydrolysed starch into a mixture of cyclodextrins and linear dextrins. For industrial production, specially selected strains of Bacillus have been used (see, Sieard & Saniez in Cyclodextrins and their Industrial Uses Duchene (ed) Editions de Sante, Paris (1987)).

Several derivatives of cyclodextrins have been synthesized and are commercially available. The 18 to 24 hydroxyl groups of the respective cyclodextrin molecules are the starting points for the synthesis of such derivatives. The differences in reactivity between the alcohol groups are usually sufficiently large to induce some selectivity (Sebille in Cylodextrins and their Industrial Uses Duchene (ed) Editions de Sante, Paris (1987)) 1987). Using known methods, methyl-, ethyl-, hydroxyethyl-, hydroxymethyl-, and hydroxypropyl-substituted cyclodextrins can be produced.

The physico-chemical properties of the cyclodextrin derivatives depend strongly on the kind and the degree of substitution. For example, their solubility in water ranges from insoluble (e.g., triacetyl-$\beta$-cyclodextrin) to 147% soluble (w/v) (G-2-$\beta$-cyclodextrin). In addition, they are soluble in many organic solvents. The properties of the cyclodextrins enable the control over solubility of various formulation components (e.g., growth factors) by increasing or decreasing their solubility.

The concentration of the cyclodextrins in the tissue culture media of the invention is typically at least about 0.1% (w/v), often at least about 1%, usually at least about 1.25%, and more usually 2.5%. The upper limit for the cyclodextrin concentration is usually about 10%, and often about 5%.

Without wishing to be bound by theory, it is believed that cyclodextrins are useful in controlling solubility of insoluble components in the plant tissue culture medium. In addition, the cyclodextrins help adjust the osmolality of the medium to maintain proper turgor pressure in the cells. These compounds have a number of other effects in plant tissue media, including providing bacteriostatic effects, stabilizing biologically active and volatile substances in the medium, protecting against oxidation, and the like. As a result of these and other effects, cyclodextrins increase cell viability, cell division, cellular development and other parameters of cell tissue culture growth. In addition, cyclodextrins can increase production of secondary metabolites.

Tissue cultures are established according to well known standard techniques. Typically, the plant material is surface-sterilized prior to introducing it to the culture medium. Any conventional sterilization technique, such as chlorinated bleach treatment can be used. In addition, antimicrobial agents may be included in the growth medium. Under appropriate conditions plant tissue and cells form callus, which may be grown either as solid tissue on solidified medium or as a cell suspension in a liquid medium. Secondary metabolic products of the callus may be isolated from the callus cells or from the culture medium using known techniques (see, e.g., U.S. Pat. No. 5,019,504).

As noted above, of particular interest to the present invention is the culture of Taxus cells for the recovery of taxol and related taxanes. Establishment of Taxus cultures and isolation of taxanes is described in U.S. Pat. No. 5,019,504. Haploid derived Taxus cell suspension cultures and a medium for their growth (DV medium) are described in Durzan and Ventimiglia In Vitro Cell Dev. Biol. 30:219–227 (1994) and in U.S. Ser. No. 08/277,463.

To establish haploid cultures, young strobili are collected after the female gametophyte is formed. The immature strobili are preferably collected no later than several weeks after fertilization. The material is surface-sterilized according to well-known methods. Standard aseptic conditions are preferably used after cultures are established. Isolated female gametophytes are cut to increase surface area. Gametophytes bearing embryos should be carefully identified and dissected to remove all traces of embryonic (diploid) cells so as not to inadvertently recover diploid cells. Haploid cell line recovery may be confirmed by explant location, size, staining reactions and by actually counting chromosomes in cell samples.

Haploid cells proliferate on selective media (preferably semi-solid) to produce a callus of haploid cell types and their derivatives. Since all recessive genes are expressed, many gametophytic cells may die if they contain lethal genes. The surviving cells grow into a white callus that ages and browns if subculture schedules are not maintained. The best subculture rates for scale-up are at least weekly. Once established, the haploid callus may be grown as a cell culture with cells being immobilized in a bioreactor or as a cell suspension culture using many of the available bioreactor designs.

For the recovery and scale-up of haploid cells, a medium which substantially lacks nitrates is preferably used. It is understood that modifications can be made in these media, such as substitutions of salts, e.g., addition or deletion of various components or alteration of proportions. For example, increased nitrogen (in the form of urea or arginine) increases the growth rate. Thus it is apparent that determination of suitable and optimal media for particular cells would be within the ability of a person skilled in the art.

The culture media used in the methods of the invention may be solid, semi-solid or liquid. Any gelling agent (e.g., agar, Gelrite and the like) commonly used to solidify media can be used. For establishment of cell suspension cultures, an inoculation density of about 1 gm per 100 ml medium is preferably used. Cells are subcultured every 10 to 14 days or sooner to scale-up for cell mass.

Culture conditions are optimized for the steady-state production of taxanes. Culture conditions typically include low light conditions, preferably darkness, to maintain heterotrophic growth and preserve the development and integrity of haploid cells. Temperature, air pressures and gaseous atmospheres can be varied as necessary to approximate conditions found in the seed.

Taxanes may be recovered according to standard techniques, for example, as described in U.S. Pat. No. 5,019,504. Adsorbent beads may be used to remove the taxanes produced. In addition, particulate matter released by the cells may be used to adsorb the taxanes. The particular adsorbent material is not a critical aspect of the invention, so long as the material provides a sink for removing the end-product from the reaction sequence.

Although not essential, taxane production can be induced by the addition of various elicitors. Such compounds include fungal elicitors, vanadyl sulfate, 3,4-dichlorophenoxy triethyl(amine), and the like which generally stimulate production of secondary products in plant cells.

EXAMPLE 1

This example demonstrates that use of cyclodextrins in plant tissue culture media increases growth of plant cells.

Norway spruce suspension culture in ½ L.P. medium supplemented with 5 different cyclodextrins were evaluated for increased fresh weight after growth in darkness at 20° C.±2° during a 2 week period. Each culture was inoculated with 0.25 g fresh weight of cells in 50 ml of culture medium. The results are presented in Table 1.

TABLE 1

| Cyclodextrin | Concentration (%) | | | |
|---|---|---|---|---|
| | 1.25 | 2.50 | 5.00 | 10.00 |
| Hydroxyethyl-β-cyclodextrin | 2.15 (+79) | 1.80 (+50) | 1.97 (+64) | 1.08 (−10) |
| G2-α-cyclodextrin | 1.66 (+38) | 2.09 (+73) | 1.59 (+33) | 1.60 (+33) |
| G2-β-cyclodextrin | 2.71 (+125) | 2.14 (+78) | 1.68 (+40) | 0.28 (−77) |
| Hydroxypropyl-β cyclodextrin | 1.60 (+33) | 1.35 (+13) | 1.28 (+7) | 0.75 (−38) |
| Methyl-β-cyclodextrin | 1.85 (+54) | 1.73 (+44) | 1.71 (+43) | 0.95 (−21) |
| | | No Cyclodextrins added | | |
| Replicate controls: | 1.21 | 1.54 | 0.92 | 1.13 |
| | | Average Control: 1.20 | | |

All values are: grams fresh weight of tissue
() values: % increase or decrease from the average control value In conclusion, all cyclodextrins improved the recovery of cultures. G2-β-cyclodextrin appeared to be the best at 1.25% (w/v).

EXAMPLE 2

This example shows the effects of a broad range of cyclodextrins (all of which are available from Ensuiko Sugar Refining Co., Tokyo, Japan) on growth of Norway spruce tissue culture cells. The following cyclodextrins were used:

| | | |
|---|---|---|
| α-cyclodextrin | β-cyclodextrin | γ-cyclodextrin |
| G2-α-cyclodextrin | G2-β-cyclodextrin | Isoeleat-cyclodextrin |
| Dexy Pearl α-100 cyclodextrin | Dexy Pearl β-cyclodextrin | |
| Methyl-β-cyclodextrin | Hydroxyethyl-β- | |

| | |
|---|---|
| Hydroxypropyl-β-cyclodextrin | cyclodextrin |

Each cyclodextrin was tested in triplicate at the following concentrations: 0, 0.00001, 0.0001, 0.001, 0.01, 0.1, 1.0 & 10.0 grams per 100 ml of media. The results indicated overall growth improvement with the various beta cyclodextrins especially G2-beta cyclodextrin. In this experiment, the α and γ cyclodextrins were not as effective. However, α-cyclodextrin did cause morphological changes in the Norway spruce suspensor masses. At 10 grams per 100 ml of media, α-cyclodextrin inhibited suspensor formation in the embryonal suspensor masses and altered their cellular appearance. The normally clear and transparent embryonal cells were transformed to a milky white appearance by the 10% α-cyclodextrin. The change in opacity of the cells may be due to changes in carbohydrate composition of the cell wall. The lack of suspensor cells in the 10% G2-β-cyclodextrin treatment indicates a block in the developmental path of the cells giving rise to the suspensors.

EXAMPLE 3

This example shows the effect of G2-β-cyclodextrin on growth of *Taxus brevifolia* female gametophytic tissue grown on DV semisolid medium as described in Durzan and Ventimiglia In Vitro Cell Dev. Biol. 30:219–227 (1994). These results indicate that the cyclodextrin can act as an elicitor of secondary metabolites. Cultures exposed to 1 % (w/v) G-2 β-cyclodextrin manufactured compounds which diffused into the medium and colored it a dark red. When moved to media not containing the cyclodextrin, the cultures immediately stopped producing the red compounds. Exposure to the cyclodextrin also caused the gametophytic tissues to turn a dark red to brown color.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of making a cell or tissue culture plant nutrient formulation comprising cyclodextrin, the method comprising:
   adding free cyclodextrin to a cell or tissue culture plant nutrient formulation to a final concentration of between about 0.1% and about 10% (w/v).

2. The method of claim 1, wherein the plant nutrient formulation is a tissue culture medium.

3. The method claim 2, wherein the tissue culture medium is ½ L.P. medium.

4. The method of claim 1, wherein the cyclodextrin is hydroxyethyl-β-cyclodextrin.

5. The method of claim 1, wherein the cyclodextrin is G2-αcyclodextrin.

6. The method of claim 1, wherein the cyclodextrin is G2-βcyclodextrin.

7. The method of claim 1, wherein the cyclodextrin is hydroxypropyl-β-cyclodextrin.

8. The method of claim 1, wherein the cyclodextrin is methyl-β-cyclodextrin.

9. The method of claim 1, wherein the final concentration of the cyclodextrin is between about 1.25% and about 5% (w/v).

10. A cell or tissue culture plant nutrient formulation made according the method of claim 1.

11. A method of growing a cell or tissue culture, the method comprising contacting the cell or tissue culture with a cell or tissue culture plant nutrient formulation of claim 10; and maintaining the cell or tissue culture under conditions suitable for growth.

12. The method of claim 11, wherein the plant consists of plant tissue culture cells.

13. The method of claim 12, wherein the plant tissue culture cells are from a member of the order Coniferales.

14. The method of claim 12, wherein the plant tissue culture cells are from Picea.

15. The method of claim 12, wherein the plant tissue culture cells are from Taxus.

16. A cell or tissue culture plant nutrient formulation comprising free cyclodextrin at a concentration between about 0.1% and about 10% (w/v).

17. The cell or tissue culture plant nutrient formulation of claim 16, which is ½ L.P. medium.

18. The cell or tissue culture plant nutrient formulation of claim 16, wherein the cyclodextrin is hydroxyethyl-β-cyclodextrin.

19. The cell or tissue culture plant nutrient formulation of claim 16, wherein the cyclodextrin is G2-α-cyclodextrin.

20. The cell or tissue culture plant nutrient formulation of claim 16, wherein the cyclodextrin is G2-β-cyclodextrin.

21. The cell or tissue culture plant nutrient formulation of claim 16, wherein the cyclodextrin is hydroxypropyl-β-cyclodextrin.

22. The cell or tissue culture plant nutrient formulation of claim 16, wherein the cyclodextrin is methyl-β-cyclodextrin.

23. The cell or tissue culture plant nutrient formulation of claim 16, wherein the cyclodextrin is at a concentration between about 1.25% and about 5% (w/v).

* * * * *